United States Patent
Lema et al.

(10) Patent No.: US 10,532,017 B2
(45) Date of Patent: Jan. 14, 2020

(54) STABLE ANTIOXIDANT COMPOSITIONS

(71) Applicant: L'OREAL, Paris (FR)

(72) Inventors: Lisa Yarhyna Lema, Bronx, NY (US); Valerie Robert, Paris (FR); Jodi Goldberg, Springfield, NJ (US); Geoffrey Genesky, Paris (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 15/779,272

(22) PCT Filed: Dec. 27, 2016

(86) PCT No.: PCT/US2016/068662
§ 371 (c)(1),
(2) Date: May 25, 2018

(87) PCT Pub. No.: WO2017/117099
PCT Pub. Date: Jul. 6, 2017

(65) Prior Publication Data
US 2018/0325792 A1 Nov. 15, 2018

Related U.S. Application Data

(60) Provisional application No. 62/272,326, filed on Dec. 29, 2015, provisional application No. 62/272,291, filed on Dec. 29, 2015.

(51) Int. Cl.
*A61K 8/06* (2006.01)
*A61Q 19/08* (2006.01)
(Continued)

(52) U.S. Cl.
CPC .............. *A61K 8/60* (2013.01); *A61K 8/06* (2013.01); *A61K 8/342* (2013.01); *A61K 8/345* (2013.01);
(Continued)

(58) Field of Classification Search
CPC ............ A61K 31/7016; A61K 2300/00; A61K 2800/48; A61K 2800/522; A61K 8/06;
(Continued)

(56) References Cited

U.S. PATENT DOCUMENTS 6,596,761 B2  7/2003  Lanzendorfer et al.
8,765,693 B2  7/2014  Potin et al.
(Continued)

FOREIGN PATENT DOCUMENTS

CA    2247645 C    9/2007
DE    29522375 U1  8/2002
(Continued)

OTHER PUBLICATIONS

M. Simmons; "Neohesperidin dihydrochalcone sources, health benefits and uses" [online] retrieved from: https://www.naturalpedia.com/neohesperidin-dihydrochalcone-sources-html; Oct. 5, 2017; 5 pages. (Year: 2017).*
(Continued)

*Primary Examiner* — Ernst V Arnold
(74) *Attorney, Agent, or Firm* — Polsinelli PC

(57) ABSTRACT

The present disclosure relates to antioxidant compositions comprising a high amount of stabilized neohesperidin dihydrochalcone. The antioxidant compositions may further include additional antioxidants, such as ferulic acid, and tocopherols. The compositions include at least 20 wt. % of one or more water-soluble solvents, such as propanediol, which contribute to the surprising solubility and stability of the compositions. The antioxidant properties of the compositions make them particularly effective for treating and protecting the skin. For example, the compositions are useful for protecting the skin from environmental insult.

21 Claims, 2 Drawing Sheets

(51) Int. Cl.
    *A61K 8/60*    (2006.01)
    *A61K 8/34*    (2006.01)
    *A61K 8/365*   (2006.01)
    *A61K 8/67*    (2006.01)
    *A61K 8/73*    (2006.01)
    *A61K 8/92*    (2006.01)

(52) U.S. Cl.
    CPC .............. *A61K 8/365* (2013.01); *A61K 8/678* (2013.01); *A61K 8/737* (2013.01); *A61K 8/92* (2013.01); *A61Q 19/08* (2013.01); *A61K 2800/48* (2013.01); *A61K 2800/522* (2013.01)

(58) Field of Classification Search
    CPC ........ A61K 8/342; A61K 8/345; A61K 8/365; A61K 8/60; A61K 8/602; A61K 8/678; A61K 8/73; A61K 8/737; A61K 8/92; A61Q 17/00; A61Q 19/00; A61Q 19/08
    See application file for complete search history.

(56) References Cited

U.S. PATENT DOCUMENTS

2004/0258654 A1    12/2004   Nielsen
2012/0064022 A1*   3/2012    Wray ..................... C08G 77/50
                                                            424/70.12
2014/0107048 A1*   4/2014    Pan ........................ A61Q 19/00
                                                            514/27

FOREIGN PATENT DOCUMENTS

FR         2942962 A1      9/2010
FR         2946253 A1      12/2010
WO         2015044080 A1   4/2015

OTHER PUBLICATIONS

International Search Report and Written Opinion dated Mar. 17, 2017 in corresponding PCT Application No. PCT/US2016/068662.
Supplementary European Search Report dated Jul. 16, 2019 for corresponding European Application No. EP 16 88 2493.

Borrego et al., "Neohesperidin Dihydrochalcone. State of Knowledge", vol. 200, No. 1, 1995, pp. 32-37 XP000917617.

* cited by examiner

STABLE ANTIOXIDANT COMPOSITIONS

CROSS-REFERENCE TO RELATED APPLICATIONS

This application is a national stage application (under 35 U.S.C. § 371) of PCT/US2016/068662, filed Dec. 27, 2016, which claims benefit of U.S. Provisional Applications Nos. 62/272,326, filed Dec. 29, 2015, and 62/272,291, filed Dec. 29, 2015, respectively, which are incorporated herein by reference in their entireties.

FIELD OF THE DISCLOSURE

The present disclosure relates to stable antioxidant compositions. The compositions contain a unique blend of antioxidants including neohesperidin dihydrochalcone, at optimal concentrations for protecting human skin from environmental stressors and atmospheric impact.

BACKGROUND

Environmental pollution conditions are fast worsening and becoming more apparent in the daily life of consumers worldwide. The damage of pollution against human skin is also becoming more and more evident. Human skin is subjected to a variety of insults by extrinsic factors such as ultraviolet (UV) radiation, environmental pollution, wind, heat, infrared radiation, low humidity, harsh surfactants, abrasives, etc. Recent studies suggest that in addition to UV radiation, other environmental factors contribute to the development of solar lentigines, particularly air pollution. Ultimately, these factors result in visible signs of skin damage including small brown patches on the skin, especially in the elderly.

Typical skin damage includes fine lines, wrinkling, hyperpigmentation, sallowness, sagging, dark under-eye circles, puffy eyes, enlarged pores, visible dead skin i.e., flaking, scaling, dryness, and roughness. In addition to skin damage, environmental pollution can also cause discomfort such as irritation, itching, dryness, roughness, allergy, etc. Suppressing reactive oxygen species might be the key in the protection against pollution. For example, exhaust particulates and smoke can upregulate matrix metalloproteins, thereby impacting the integrity of the skin.

Antioxidants are chemicals and biologicals that destroy harmful oxygen free radicals. Examples of Antioxidants include vitamins E, C, D, A, ferulic acid, neohesperidin dihydrochalcone, glutathione, melatonin, metallic zinc, beta-carotene, and numerous other compounds. Antioxidants scavenge oxidation of cells caused by oxygen free radicals, thereby preventing cell damage. In order to be active, the antioxidants must be in a reduced form. However, it can be difficult for antioxidants to maintain a completely reduced state during manufacturing, storage, transportation, and maintenance. In particular, neohesperidin dihydrochalcone is known to be difficult to incorporate into acceptable cosmetic formulation due to its ease of oxidation and problems associated with stability. Currently, there are no commercial products on the market with high levels of neohesperidin dihydrochalcone. The maximum level documented in a stable emulsion is 0.613%. Accordingly, there is a need for products containing higher amounts of stabilized neohesperidin dihydrochalcone.

SUMMARY OF THE DISCLOSURE

The present disclosure relates to antioxidant compositions comprising a high amount of stabilized neohesperidin dihydrochalcone. The antioxidant compositions may further include additional antioxidants, such as ferulic acid, and tocopherols. The compositions include at least 20 wt. % of one or more water-soluble solvents, such as propanediol, which contribute to the surprising solubility and stability of the compositions. The antioxidant properties of the compositions make them particularly effective for treating and protecting the skin. For example, the compositions are useful for protecting the skin from environmental insult and for preventing or minimizing the effects of environmental damage and ageing.

The antioxidant compositions are typically emulsions that are appropriate for topical application to the skin, for example, to the skin of the face. The compositions typically include: (a) neohesperidin dihydrochalcone, and optionally one or more additional antioxidants; (b) about 1 wt. % to about 30 wt. % by weight of one or more of fatty compounds; (c) about 0.1 wt. % to about 2 wt. % by weight of one or more natural thickeners; (d) at least 20 wt. % of water-soluble solvent selected from one or more $C_{3-10}$ alkanediols, and optionally glycerin; (e) about 1 wt. % to about 15 wt. % by weight of one or more emulsifiers; (f) optionally, one or more natural active compounds; and (g) water.

A unique aspect of these compositions is their ability to solubilize and stabilize high amounts neohesperidin dihydrochalcon in addition to other optional antioxidants. The compositions can contain, for example, from about 0.9 wt. % to about 1.1 wt. % of solubilized and stabilized neohesperidin dihydrochalcone, based on the total weight of the antioxidant composition. Additional antioxidants may also be included, for example, ferulic acid and tocopherols (natural tocopherol blend). The total amount of all antioxidants (including the neohesperidin dihydrochalcone) in the antioxidant compositions, may be from about 0.9 wt. % to about 5 wt. %, based on the total weight of the antioxidant composition.

The water-soluble solvent typically includes one or more $C_{3-10}$ alkanediols. For example, in some cases, at least one of the water-soluble solvents is 1,3-propanediol, which may optionally be in an amount of at least 15 wt. % to about 20, 30, or 40 wt. %. One or more additional $C_{3-10}$ alkanediols may also be present, including, for example, 1,2-octanediol (caprylyl glycol). In addition to the one or more $C_{3-10}$ alkanediols, the compositions may optionally include glycerin as a water-soluble solvent.

Emulsifiers, typically in an amount of about 1 wt. % to about 15 wt. %, or about 5 wt. % to about 12 wt. %, can be used to form stable emulsions. Emulsions are useful for holding the desired amount of antioxidants in an aqueous phase and/or a fatty phase (depending on the solubility of the particular antioxidant). The emulsions are particularly stable and therefore remain homogenous, without exhibiting visible signs of crystal formation or phase-separation for at least 2 weeks, preferably at least 1 month, or more preferably at least two months.

The antioxidant compositions are useful in methods for treating damaged skin, for improving the health and/or appearance of skin, and for preventing or minimizing environmental impact and damage to the skin. Due the antioxidant properties of the compositions, the compositions may be applied to the skin in methods for improving the radiance of the skin, in methods for improving the evenness of skin tone, in methods for improving the clarity of the skin, and/or in methods for improving the overall appearance of the skin. Further, the compositions are useful in methods for protecting the skin from and/or minimizing the effects of environmental stress and environmental pollution. The methods typically involve applying the compositions to the skin, for example, the face. The compositions may be applied once, or may be applied repeatedly over a period of time. For example, the compositions may be applied once a day, twice a day, three times a day, (or applied each night before bed), for at least one week, for at least two weeks, or longer.

BRIEF DESCRIPTION OF THE DRAWINGS

Implementation of the present technology will now be described, by way of example only, with reference to the attached figures, wherein.

Figure 1:
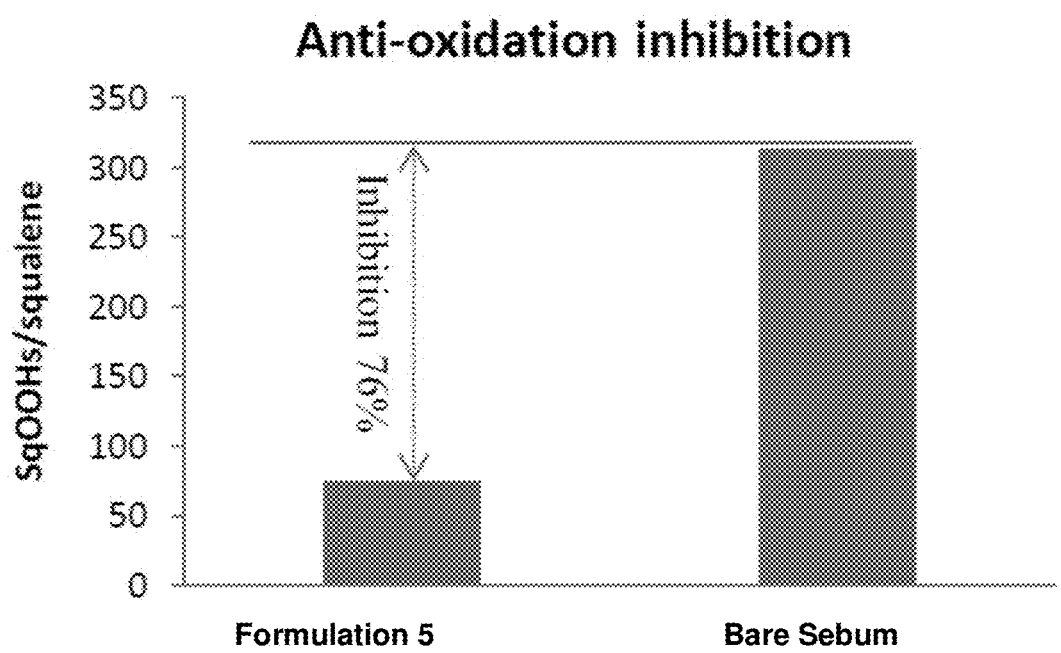
FIG. 1 is a graph showing the antioxidant properties provided by a formulation of the instant disclosure in an ex-vivo test.

It should be understood that the various aspects are not limited to the arrangements and instrumentality shown in the drawings.

DETAILED DESCRIPTION OF THE DISCLOSURE

The antioxidant compositions of the instant disclosure are typically in the form of an emulsion, are stable, and include neohesperidin dihydrochalcone, in addition to other optional antioxidants. More specifically, the antioxidant compositions typically include:

(a) neohesperidin dihydrochalcone, and optionally one or more additional antioxidants;
(b) about 1 wt. % to about 30 wt. % by weight of one or more of fatty compounds;
(c) about 0.1 wt. % to about 2 wt. % by weight of one or more natural thickeners;
(d) at least 20 wt. % of water-soluble solvent selected from one or more $C_{3-10}$ alkanediols, and optionally glycerin;
(e) about 1 wt. % to about 15 wt. % by weight of one or more emulsifiers;
(f) optionally, one or more natural active compounds; and
(g) water.

The total amount of the neohesperidin dihydrochalcone is usually at least 0.1 wt. % up to about 2, 3, or 4 wt. %, based on the total weight of the antioxidant composition. In some cases, the total amount of the neohesperidin dihydrochalcone is at least 0.5 wt. % up to about 1, 2, or 3 wt. %. In particular, however, the total amount of the neohesperidin dihydrochalcone is about 0.9 wt. % to about 1.1 wt. %; or about 1 wt. %.

Additional antioxidants may also be included in the antioxidant compositions. For instance, in some case, the composition may include ferulic acid. The ferulic acid may be present in an amount of about 0.01 wt. % to about 1, 2, or 3 wt. %, based on the total weight of the antioxidant composition. In some cases, the total amount of ferulic acid may be about 0.05 wt. % to about 1, 2, or 3 wt. %, or may be about 0.1 wt. % to about 1 or 2 wt. %. Furthermore, the total amount of ferulic acid may be about 0.1 wt. % to about 1 wt. % or about 0.1 wt. % to about 0.5 wt. %.

Tocopherols may be included as an antioxidant. A natural tocopherol blend is preferred. The tocopherols may be present in an amount of about 0.01 wt. % to about 3, 4, or 5 wt. %, based on the total weight of the antioxidant composition. In some cases, the total amount of tocopherols is about 0.1 wt. % to about 3, 4, or 5 wt. %, or about 0.2 wt. % to about 2 wt %, or about 0.5 wt. % to about 1.5 wt. %.

In some cases both ferulic acid and tocopherols are included in the antioxidant compositions with the neohesperidin dihydrochalcone. When multiple antioxidants are included in the compositions (regardless of whether the additional antioxidants are ferulic acid and/or tocopherols), the total amount of the antioxidants is typically no more than about 5, 10, or 15 wt. % of the composition. For instance, the total amount of the antioxidants may be about 1 wt. % to about 15 wt. %, about 1 wt. % to about 10 wt. %, about 1 wt. % to about 8 wt. %, about 1 wt. % to about 6 wt. %, about 1 wt. % to about 5 wt. %, about 1 wt. % to about 4 wt. %, or about 1 wt. % to about 3 wt. %, based on the total weight of the antioxidant composition.

The antioxidant compositions include one or more fatty compounds. These fatty substances may be of animal, plant, mineral or synthetic origin. For example, the fatty compounds may include natural oils of vegetable, animal or marine origin, synthetic oils, mineral oils, hydrogenated oils, silicone oils, hydrocarbon-based compounds, saturated or unsaturated fatty acids, fatty acid esters, liquid waxes, fatty alcohols, and a mixture thereof. In some cases, the one or more fatty compounds are natural fatty compounds. For example, the one or more fatty compounds may be natural vegetable oils. Non-limiting examples of natural vegetable oils include shea butter, apricot kernel oil, rice bran oil, olive oil, and mixtures thereof.

The total amount of the one or more fatty compounds is typically about 1 wt. % to about 30 wt. %, based on the total weight of the antioxidant composition. In some cases, the total amount of the one or more fatty compounds is about 1 wt. % to about 25 wt. %, about 1 wt. % to about 20 wt. %, about 1 wt. % to about 15 wt. %, about 5 wt. % to about 30 wt. %, about 5 wt. % to about 25 wt. %, about 5 wt. % to about 20 wt. %, or about 5 wt. % to about 15 wt. %.

As mentioned above, the antioxidant compositions often include at least 20 wt. % of water-soluble solvent, wherein the water soluble solvent includes one or more $C_{3-10}$ alkanediols, and optionally glycerin. Non-limiting examples of $C_{3-10}$ alkanediols include 1,2-propanediol, 1,3-propanediol, 1,2-butanediol, 1,3-butanediol, 1,4-butanediol, 2,3-butanediol, 1,2-pentanediol, 1,4-pentanediol, 1,5-pentanediol, 2,4-pentanediol, 1,2-hexanediol, 1,5-hexanediol, 1,6-hexanediol, 2,5-hexanediol, 1,7-heptanediol, 1,2-octanediol, 1,8-octanediol, 1,9-nonanediol, 1,2-decanediol, 1,10-decanediol, neopentyl glycol, and mixtures thereof.

In some instances, the antioxidant compositions include at least 1,3-propanediol. Likewise, in some cases, when the compositions include 1,3-propanediol, the total amount of the 1,3-propanediol is at least 15 wt. %, based on the total weight of the antioxidant composition. The total amount of the 1,3-propanediol may be about 15 wt. % to about 30 wt. %, about 15 wt. %, to about 25 wt. %, about 15 wt. % to about 20 wt. %.

In some cases, the antioxidant compositions include, in addition to 1,3-propandiol, one or more additional $C_{3-10}$ alkanediols, for example 1,2-octanediol (caprylyl glycol). The one or more additional $C_{3-10}$ alkanediols may be in an amount of about 0.01 wt. % to about 10 wt. %, about 0.01 wt. % to about 5 wt. %, about 0.01 wt. % to about 3 wt. %, about 0.01 wt. % to about 1 wt. %, about 0.05 wt. % to about 5 wt. %, about 0.05 wt. % to about 3 wt. %, about 0.05 wt. % to about 2 wt. %, about 0.05 wt. % to about 1 wt. %, about 0.1 wt. % to about 5 wt. %, about 0.1 wt. % to about 3 wt. %, or about 0.1 wt. % to about 1 wt. %, based on the total weight of the antioxidant composition.

In some cases, the antioxidant compositions include, in addition to one or more $C_{3-10}$ alkanediols (for example, in addition to 1,3-propanediol), glycerin. The total amount of the glycerin in the antioxidant composition may be about 1 wt. % to about 20 wt. %, about 1 wt. % to about 15 wt. %, about 1 wt. % to about 10 wt. %, about 1 wt. % to about 8 wt. %, about 2 wt. % to about 20 wt. %, about 2 wt. % to about 15 wt. %, about 2 wt. % to about 10 wt. %, about 2 wt. % to about 8 wt. %, about 3 wt. % to about 10 wt. %, or about 3 wt. % to about 9 wt. %, based on the total weight of the antioxidant composition.

One or more thickeners are typically included in the antioxidant compositions in order to provide an appropriate viscosity/thickness. The thickeners may also contribute to a pleasant texture and/or feel. Natural thickeners are preferred and in particular, useful thickeners include polysaccharide thickeners. Non-limiting examples of polysaccharide thickeners include gellan gum, xanthan gum, rhamsan gum, welan gum, carrageenan, guar gum, locust bean gum, tragacanth gum, succinoglucan gum, and mixtures thereof.

In some cases, the one or more thickeners comprise one or more gums. Non-limiting examples of gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *Sclerotium* gum, sodium carboxymethyl dextran, sodium carrageenan, tragacanth gum, xanthan gum, and mixtures thereof.

As mentioned previously, the antioxidant compositions are typically in the form of an emulsion. Accordingly, the compositions include one or more emulsifiers. Various emulsifiers and known, including nonionic, anionic, and cationic emulsifiers, of which may be useful in the antioxidant compositions. In some cases, the antioxidant compositions include one or more glucoside emulsifiers. Non-limiting examples of glucoside emulsifiers include cetearyl glucoside, cocoyl ethyl glucoside, disodium coco-glucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, and mixtures thereof.

In some cases, the antioxidant compositions include one or more emulsifiers that are glycerol esters of fatty acids. Non-limiting examples include glyceryl stearate, glyceryl palmitate, glyceryl arachidate and mixtures thereof. Most preferably, the glycerol ester is glyceryl stearate. More specifically, the antioxidant compositions may include one or more emulsifiers selected from the group consisting of stearic acid, cetyl alcohol, PEG-100, stearate and glyceryl stearate, cetearyl glucoside, polysorbate 20, ceteareth-20, cetyl alcohol, cetearyl alcohol, cetyl palmitate, stearyl alcohol, lecithin, hydrogenated lecithin, steareth-2, steareth-20, polyglyceryl-2 stearate, and mixtures thereof. For example, in a preferred embodiment, the antioxidant compositions include multiple emulsifiers, for example, a combination of cetearyl alcohol (and) cetearyl glucoside and glyceryl stearate.

The total amount of the one or more emulsifiers may vary, but is typically about 1 wt. % to about 20 wt. %, based on the total weight of the antioxidant composition. In some cases, the total amount of emulsifiers is about 2 wt. % to about 20 wt. %, about 2 wt. % to about 18 wt. %, about 2 wt. % to about 15 wt. %, about 3 wt. % to about 20 wt. %, about 3 wt. % to about 18 wt. %, about 3 wt. % to about 15 wt. %, about 3 wt. % to about 12 wt. %, about 5 wt. % to about 20 wt. %, about 5 wt. % to about 18 wt. %, about 5 wt. % to about 15 wt. %, about 5 wt. % to about 12 wt. %, or about 6 wt. % to about 12 wt. %.

The antioxidant compositions successfully solubilize high amounts of neohesperidin dihydrochalcone as well as other antioxidants; and the antioxidant compositions remain stable. In particular, the compositions do not phase-separate nor do they form visual crystalline particulate material. While not wishing to be bound by any particular theory, it is suspected that the surprisingly high antioxidant solubility and stability is due, at least in part, to the type(s) and amount(s) of solvent(s) used with the combination of other materials (i.e., the amount of $C_{3-10}$ alkanediols, and optionally glycerin). The antioxidant compositions remain stable for at least 2 weeks. In most cases, the antioxidant compositions remain stable for at least 1 month, at least 2 months, at least 3 months, at least 6 months, or for at least 1 year at a temperature of about 25° C.

The antioxidant compositions are typically in the form of an emulsion. The emulsions may be formed by blending the water-soluble antioxidants with water, the water-soluble solvent(s), and with one or more thickeners. This mixture may be heated and homogenized. For example, it may be heated to a temperature of about 50° C. to about 90° C., or about 60° C. to about 80° C. Separately, emulsifiers and hydrophobic compounds (the fatty substances, lipid-soluble antioxidants (e.g., tocopherols), etc.) may be combined, heated, and homogenized. For example, this fatty phase may be heated to a temperature of about 50° C. to about 90° C., or about 60° C. to about 80° C. The fatty phase can be added to the aqueous phase and homogenized to form an emulsion. For example, the combined fatty phase and aqueous phase may be homogenized for about 1 min. to about 1 hour, or about 5 min. to about 30 min. After forming the emulsion, the emulsion may be cooled, to a temperature of about 20° C. to about 60° C., or about 30° C. to about 50° C. Upon cooling, additional thickeners, emulsifiers, antioxidants, pH adjusters, vegetable extract (alpha hydroxy acid), water and/or water-soluble solvents may optionally be added, if desired, and the product mixed or homogenized. Additionally, the product may optionally be de-aerated. If needed, a pH adjuster (such as citric acid or L-arginine) can be added to bring the product to a desired pH.

In some cases, the pH of the product (the antioxidant composition) is about 4 to about 8, about 4 to about 7, about 4 to about 6, or about 4.5.

In some instances, the antioxidant compositions include:
(a) about 0.9 wt. % to about 1.1 wt. % of neohesperidin dihydrochalcone;
(b) about 1 wt. % to about 20 wt. % by weight of one or more of fatty compounds;
(c) about 0.1 wt. % to about 2 wt. % by weight of one or more natural thickeners;
(d) at least 20 wt. % of propanediol, caprylyl glycol, and glycerin;
(e) about 5 wt. % to about 15 wt. % by weight of one or more emulsifiers;
(f) optionally, one or more natural active compounds; and
(g) water.

As mentioned previously, in some cases, the antioxidant compositions may further include additional antioxidants (antioxidants in addition to neohesperidin dihydrochalcone). The additional antioxidants may be ferulic acid and tocopherols. The total amount of the antioxidants may be about 1 wt. % to about 15 wt. %, about 1 wt. % to about 10 wt. %, about 1 wt. % to about 8 wt. %, about 1 wt. % to about 6 wt. %, about 1 wt. % to about 5 wt. %, about 1 wt. % to about 4 wt. %, or about 1 wt. % to about 3 wt. %, based on the total weight of the antioxidant composition. In some cases, the antioxidant compositions include a combination of neohesperidin dihydrochalcone, ferulic acid, and tocopherols. The total amount of this particular composition may be as described above, but in a preferred embodiment, the total amount is about 1 wt. % to about 5 wt. %, preferably, about 1.2 wt. % to about 4 wt. %, or more preferably about 1.5 wt. % to about 3 wt. %, based on the total weight of the antioxidant composition (wherein about 0.9 wt. % to about 1.1 wt. % of the total combination of antioxidants is the neohesperidin dihydrochalcone).

In some instances, the antioxidant compositions include:
(a) about 0.9 wt. % to about 1.1 wt. % of neohesperidin dihydrochalcone;
(b) about 1 wt. % to about 20 wt. % by weight of one or more of fatty compounds;
(c) about 0.1 wt. % to about 2 wt. % by weight of one or more natural polysaccharide gums, wherein the one or more natural polysaccharide gums comprises xanthan gum;
(d) at least 20 wt. % of propanediol, caprylyl glycol, and glycerin;
(e) about 5 wt. % to about 15 wt. % by weight of one or more emulsifiers;
(f) optionally, one or more natural active compounds; and
(g) water.

As in other embodiments, the antioxidant compositions may further include additional antioxidants (antioxidants in addition to neohesperidin dihydrochalcone). The additional antioxidants may be ferulic acid and tocopherols. The total amount of all antioxidants may be about 1 wt. % to about 5 wt. %, preferably, about 1.2 wt. % to about 4 wt. %, or more preferably about 1.5 wt. % to about 3 wt. %, based on the total weight of the antioxidant composition.

With respect to the one or more emulsifiers, glucoside emulsifiers and glycerol esters of fatty acids are preferred. Non-limiting examples of glucoside emulsifiers include cetearyl glucoside, cocoyl ethyl glucoside, disodium cocoglucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, and mixtures thereof. Non-limiting examples of glycerol esters of fatty acids include glyceryl stearate, glycerol palmitate, glycerol arachidate and mixtures thereof. Most preferably, the glycerol ester is glyceryl stearate. In some cases, the antioxidant compositions include a mixture of emulsifiers such as a mixture of cetearyl glucoside and glyceryl stearate. In some cases the mixture includes cetearyl glucoside, glyceryl stearate, and cetearyl alcohol.

The antioxidant compositions described throughout this disclosure are useful in methods for treating damaged skin, for improving the health and/or appearance of skin, and for preventing or minimizing environmental impact and damage to the skin. The compositions may be applied to the skin in methods for improving the radiance of the skin, the evenness of skin tone, the clarity of the skin, and/or the overall appearance of the skin. The methods typically involve applying the compositions to the skin, for example, the face. The compositions may be applied once, or may be applied repeatedly over a period of time. For example, the compositions may be applied once or twice per day (or applied each night before bed), for at least one week, for at least two weeks, for at least three weeks, for at least 1 month, for at least 2 months, or longer.

More exhaustive but non-limiting lists of components useful in the antioxidants compositions of the instant disclosure are provided below.

Antioxidants

The antioxidants used may include natural exogenous phytochemical antioxidants such as phenolics and carotenoids.

The antioxidants may include flavonoids. Flavonoids constitute a large group of over 5000 polyphenolic phytochemicals with antioxidant properties that act through direct free radicals scavenging. Flavonoids have anti-inflammatory, anti-bacterial, anti-viral, anti-allergic, anti-mutagenic, anti-thrombotic, anti-neoplastic and vasodilatory action and may prevent, reduce, or eliminate the oxidative damage from dental devices using these methods of action as well. Flavonoids also exhibit chelating properties with metal ions and may reduce the oxidative damage from metal ions by sequestering the ions. Formation and stability of flavonoids-metal-chelates is a structure-dependent function. Flavonoids with a catechol moiety and with hydrogen bonds between hydroxyl group in the 5- and 3-positions have chelating properties.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, emblica *officinalis*, and bioflavonoids from rose hip and citrus may be used including watersoluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

Other antioxidants, which may be incorporated in the compositions of the present invention include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ-tocotrienol, d-delta-tocotrienol) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E and other carotenoids.

The flavonoid may be a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin.

The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin.

The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate.

The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin.

The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol.

The flavonoid may be a flavan-4-ol (derivative of 2-phenylchroman-4-ol). Flavan-4-ols include: Apiforol and Luteoforol.

The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C., and synthetic Safalcone.

The antioxidant may be a Curcuminoid. Curcuminoids include: Curcumin, Desmethoxycurcumin, bis-Desmethoxycurcumin, Tetrahydrocurcumin, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone.

The antioxidant may be a vitamin. Vitamins include: Retinol, Ascorbic acid, L-Ascorbic acid, Tocopherol, Tocotrienol, and the Vitamin cofactor: Coenzyme Q10.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, emblica *officinalis*, and bioflavonoids from rose hip and citrus may be used including watersoluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

Other antioxidants, which may be incorporated in the compositions of the present invention include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ-tocotrienol, d-delta-tocotrienol) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E and other carotenoids.

Fatty Compounds

As used herein, the term "fatty compound" is interchangeable with the term "fatty substance" and means an organic compound that is insoluble in water at ordinary temperature (25° C.) and at atmospheric pressure (760 mmHg) (e.g., has a solubility of less than 5%, for example 1%, such as 0.1%). These fatty substances may be of animal, plant, mineral or synthetic origin. For example, the fatty compounds may include natural oils of vegetable, animal or marine origin, synthetic oils, mineral oils, hydrogenated oils, silicone oils, hydrocarbon-based compounds, saturated or unsaturated fatty acids, fatty acid esters, liquid waxes, fatty alcohols, and a mixture thereof.

The term "oil" is understood to mean a compound that is liquid at room temperature (25° C.) and atmospheric pressure (1,013.25 hPa), and which is insoluble in water or is soluble to less than 10% by weight relative to the weight of oil introduced into the water at 25° C.

The term "wax" is understood to mean a fatty substance having a reversible liquid-solid change in state, which has a melting point above 30.degree. C. and generally below 90° C., and which has, in the solid state, an anisotropic crystalline arrangement.

Non-limiting examples of fatty compounds include natural oils of vegetable, animal or marine origin (such as olive oil, sesame oil, argan oil, palm oil, soybean oil, woad oil, turtle oil, babassu oil, aloe vera, avocado oil, allantoin, bisabol, grapeseed oil, apricot oil, wheatgerm oil, almond oil, *Arachis* oil, macadamia nut oil, sea buckthorn oil, evening primrose oil, borage oil, ginger oil, geraniol, jujube oil, mink oil, lanolin), synthetic oils, mineral oils (such as isohexadecane, isoparaffin, ceresin, petrolatum), hydrogenated oils, silicone oils, hydrocarbon-based compounds (such as liquid paraffin, terpenes, squalene), saturated or unsaturated fatty acids (such as myristic acid), fatty acid esters, waxes (such as whale wax, beeswax, jojoba oil which is in fact a liquid wax), fatty alcohols (such as myristyl alcohol, cetyl alcohol, stearyl alcohol, myricyl alcohol), butters (such as shea butter or cacao butter), wax esters, or a mixture thereof, lipophilic odorous compounds used in the manufacturing of fragrances, and lipophilic active ingredients.

Thickeners

Thickeners include substances that can increase the viscosity of a composition. Thickeners include those that can increase the viscosity of a composition without substantially modifying the efficacy of the active ingredient(s) within a composition. Thickeners can also increase the stability of the compositions of a composition.

Non-limiting examples of thickeners include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the cross-linking agent contains two or more carbon-carbon double bonds and is derived from a polyhydric alcohol. Examples of commercially available carboxylic acid polymers include carbomers, which are homopolymers of acrylic acid cross-linked with allyl ethers of sucrose or pentaerytritol (e.g., CARBOPOL 900 series from B. F. Goodrich).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C.sub.10-C.sub.30 straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *Sclerotium* gum, sodium carboyxmethyl dextran, sodium carrageenan, tragacanth gum, xanthan gum, and mixtures thereof.

Water-Soluble Solvent

The term "water-soluble solvent" is interchangeable with the term "water-miscible solvent" and means a compound that is liquid at 25° C. and at atmospheric pressure (760 mmHg), and it has a solubility of at least 50% in water under these conditions.

Examples of the water-soluble solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, 1,2-octanediol, 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, and sulfolane.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, and 1,2,6-hexanetriol. These may be used alone, or two or more kinds may be used together.

Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

Emulsifiers

Emulsifiers may be nonionic, anionic or cationic. Suitable emulsifying ethers and esters include ethers of polyglycols and of fatty alcohols—including saturated or unsaturated $C_{12-30}$ alcohols (e.g., oleyl alcohol, cetyl alcohol, stearyl alcohol or behenyl alcohol) and polyglycols comprising n number of oxyalkylene groups wherein n=an integer from 1 to 200 or, alternately, from 2 to 30 (e.g., 1 to 20 oxyethylene groups). Particular examples include compounds with the INCI names of steareth-n, beheneth-n or oleth-n. Suitable examples include compounds having the INCI names steareth-8, steareth-10, steareth-16, steareth-20, ceteth-10, laureth-4, laureth-3, trideceth-6, ceteareth-5, oleth-10, and beneth-10.

Esters of polyglycols and of fatty acids—including saturated or unsaturated C.sub.12-30 fatty acids (e.g., oleic acid, cetylic acid, stearic acid) and polyglycols comprising n number of oxyalkylene groups wherein n=an integer from 1 to 200 or alternately, 1 to 50 (e.g., 1 to 20 oxyethylene groups). Particular examples include compounds with the INCI name PEG-n stearate or PEG-n oleate). Suitable examples include polyethylene glycol-8 monostearate, polyethylene glycol-10, or polyethylene glycol-12 distearate.

Ethers of polyglycols and of fatty alcohols which are glycosylated—including $C_{12-30}$ alcohols having from 1 to 10 glycosyl groups and polyglycols comprising n number of oxyalkylene groups wherein n=an integer from 1 to 200 (e.g., 1 to 20 oxyethylene groups). A suitable example includes polyoxyethylenated (200E) methyl glucose distearate.

Esters of polyglycols and of fatty acids which are glycosylated—including $C_{12-30}$ fatty acids having from 1 to 10 glycosyl groups and polyglycols comprising n number of oxyalkylene groups wherein n=an integer from 1 to 200 (e.g., 1 to 20 oxyethylene groups).

Ethers of $C_{12-30}$ alcohols and of glycerol or of polyglycerol—A suitable example includes polyglyceryl-3 cetyl ether, such as CHIMEXANE NL from Chimex.

Esters of $C_{12-30}$ fatty acids and of glycerol or of polyglycerol—including esters comprising from 1 to 10 glycerol groups. Particular examples include hex-aglyceryl monosterate, diglyceryl distearate, tetraglyceryl tristearate, decaglyceryl decastearate, diglyceryl monostearate, hexaglyceryl tristearate, decaglyceryl pentastearate, the ester of glycerol and of palmitic and stearic acids, and glyceryl mono- and dibehenate.

Ethers of oxyalkylene-modified $C_{12-30}$ alcohols and of glycerol or polyglycerol may be used. Ethers of $C_{12-30}$ fatty alcohols comprising and of sucrose or of glucose—Suitable examples include compounds with the INCI names of C12-18 alkylglucoside, C12-20 alkylglucoside (e.g., MONTANOV L from Seppic), cetearyl glucoside (e.g., a mixture with cetearyl alcohol under the reference MONTANOV 68 from Seppic), myristyl glucoside (e.g., a mixture with myristyl alcohol under the reference MONTANOV 14 from Seppic) or cetearyl glucoside (e.g., TEGOCARE CG 90 from Evonik Goldschmidt), Esters of sucrose and of $C_{12-30}$ fatty acids—Particular examples include sucrose distearate or sucrose tristearate, sucrose cocoate, sucrose dilaurate, sucrose distearate, sucrose hexaerucate, sucrose hexapalmitate, sucrose laurate, sucrose mortierellate, sucrose myristate, sucrose oleate, sucrose palmitate, sucrose pentaerucate, sucrose polybehenate, sucrose polycottonseedate, sucrose polylaurate, sucrose polylinoleate, sucrose polyoleate, sucrose polypalmate, sucrose polysoyate, sucrose polystearate, sucrose ricinoleate, sucrose stearate, sucrose tetraisostearate, and sucrose trilaurate. A suitable example includes the mixture of esters (mono- and polyesters) of stearic acid and of sucrose sold as CRODESTA FI 10 by Croda.

Esters of pentaerythritol and of $C_{12-30}$ fatty acids—particular examples include pentaerythritol tetrastearate.

Esters of sorbitol and/or of sorbitan and of $C_{12-30}$ fatty acids—particular examples include sorbitan monostearate, sorbitan tristearate, or sorbitan laurate, such as SPAN 20 from Uniqema, Ethers of sorbitol and/or of sorbitan and of alkoxylated sorbitan—suitable examples include sorbeth-8 beeswax or sorbeth-20 beeswax from Nikko Chemical.

Ethers of polyglycols and of cholesterol—particular examples include choleth-3, choleth-10 (such as EMALEX CS-10 from Nihon Emulsion Company), choleth-15 (such as EMALEX CS-15 from Nihon Emulsion Company) or choleth-20 (such as EMALEX CS-20 from Nihon Emulsion Company).

Esters of $C_{12-30}$ fatty acids and of alkoxylated ethers of sorbitol and/or of Suitable examples include polysorbate-60, polysorbate-61, sorbeth-3 isostearate, polyoxyethylenated 4 OE sorbitan monostearate, and polyoxyethylenated 200E sorbitan tristearate.

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu. Exemplary materials include materials with the following International Nomenclature of Cosmetic Ingredients (INCI) designations: Bis-Butyldimethicone Polyglyceryl-3; Bis-PEG/PP G-14/14 Dimethicone;

Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; and mixtures thereof.

Emulsifiers also include emulsifying silicone elastomers. Suitable emulsifying silicone elastomers may include at least one polyalkyl ether or polyglycerolated unit. These cross-linked elastomers may also be co-modified to include alkyl substituents. Polyoxyalylenated emulsifying silicone elastomers that may be used in at least one embodiment of the invention include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other silicone emulsifying elastomers are supplied by Dow Corning™, including PEG-12 dimethicone crosspolymers (DC 9010 and 9011). Other suitable silicone emulsifiers sold by Dow Corning include DC9010 and DC9011.

Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

Another suitable crosslinked silicone elastomer emulsifier is dimethicone/PEG-10/15 crosspolymer, which provides excellent aesthetics due to its elastomeric backbone, but also excellent emulsification properties. Further examples of crosslinked organosiloxane emulsifiers include, but are not limited to dimethicone/dimethicone PEG/PPG 15 crosspolymer; dimethicone PEG-10 crosspolymer; dimethicone PEG-10/15 crosspolymer; dimethicone PEG-15 crosspolymer; dimethicone polyglycerin-3 crosspolymer; dimethicone PPG-20 crosspolymer; lauryl dimethicone PEG-15 crosspolymer; lauryl dimethicone polyglycerin-3 crosspolymer; PEG-8 dimethicone polysorbate-20 crosspolymer; PEG-10 dimethicone/vinyl dimethicone crosspolymer; PEG-10 lauryl dimethicone crosspolymer; PEG-15/lauryl dimethicone crosspolymer; PEG-15 laurylpolydimethylsiloxy ethyl crosspolymer; and mixtures thereof.

The group of nonionic emulsifiers includes, for example, (1) products of the addition of 2 to 50 mol ethylene oxide and/or 1 to 20 mol propylene oxide onto linear fatty alcohols containing 8 to 40 carbon atoms, onto fatty acids containing 12 to 40 carbon atoms and onto alkylphenols containing 8 to 15 carbon atoms in the alkyl group;

(2) $C_{12-18}$ fatty acid monoesters and diesters of products of the addition of 1 to 50 mol ethylene oxide onto glycerol;

(3) sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) products of the addition of 7 to 60 mol ethylene oxide onto castor oil and/or hydrogenated castor oil;

(6) polyol esters and, in particular, polyglycerol esters, such as, for example, polyolpoly-12-hydroxystearate, polyglycerol polyricinoleate, polyglycerol diisostearate or polyglycerol dimerate, as well as mixtures of compounds from several of these classes;

(7) products of the addition of 2 to 15 mol ethylene oxide onto castor oil and/or hydrogenated castor oil;

(8) partial esters based on linear or branched, unsaturated or saturated $C_{6-22}$ fatty acids, ricinoleic acid and 12-hydroxystearic acid and polyglycerol, pentaerythritol, dipentaerythritol, sugar alcohols (for example, sorbitol), alkyl glucosides (for example, methyl glucoside, butyl glucoside, and lauryl glucoside) and polyglucosides (for example, cellulose) or mixed esters, such as glyceryl stearate citrate and glyceryl stearate lactate, for example;

(9) polysiloxane/polyalkyl polyether copolymer or corresponding derivatives; (10) mixed esters of pentaerythritol, fatty acids, citric acid and fatty alcohol and/or mixed esters of fatty acids containing 6 to 22 carbon atoms, methyl glucose and polyols, preferably glycerol or polyglycerol.

The addition products of ethylene oxide and/or propylene oxide onto fatty alcohols, fatty acids, alkylphenols, glycerol monoesters and diesters, and sorbitan monoesters and diesters of fatty acids, or onto castor oil are known commercially-available products. They are homolog mixtures of which the average degree of alkoxylation corresponds to the ratio between the quantities of ethylene oxide and/or propylene oxide and substrate with which the addition reaction is carried out. These emulsifiers are water-in-oil (w/o) or oil-in-water (o/w) emulsifiers, depending on the degree of ethoxylation. C.sub.12/18 fatty acid monoesters and diesters of addition products of ethylene oxide onto glycerol are known as lipid layer enhancers for cosmetic preparations.

In some cases, particularly suitable and mild emulsifiers are the polyol poly-12-hydroxystearates and mixtures thereof marketed by Cognis Deutschland GmbH under the name of "DEHYMULS PGPH" (w/o emulsifier) or "EUMULGIN VL 75" (mixture with Coco Glucosides in a ratio by weight of 1:1, o/w emulsifier) or "DEHYMULS SBL" (w/o emulsifier). The polyol component of these emulsifiers may be derived from substances which contain at least two, preferably 3 to 12, and more particularly 3 to 8 hydroxyl groups, and 2 to 12 carbon atoms.

In principle, suitable lipophilic w/o emulsifiers are emulsifiers with an HLB value of 1 to 8 which are listed in numerous Tables and are well-known to the practitioner. Some of these emulsifiers are listed, for example, in Kirk-Othmer, Encyclopedia of Chemical Technology, 3rd Edition, 1979, Vol. 8, page 913. The HLB value for ethoxylated products may also be calculated to the following formula: HLB=(100−L): 5, where L is the percentage by weight of lipophilic groups, i.e., fatty alkyl or fatty acyl groups, in percent by weight in the ethylene oxide adducts.

Of particular advantage from the group of w/o emulsifiers are partial esters of polyols, more particularly $C_{4-6}$ polyols, such as, for example, partial esters of pentaerythritol or sugar esters, for example, sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable emulsifiers.

Depending on the formulation, it can be of advantage additionally to use at least one emulsifier from the group of nonionic o/w emulsifiers (HLB value: 8-18) and/or solubilizers. Examples of such emulsifiers are the ethylene oxide adducts mentioned at the beginning with a correspondingly high degree of ethoxylation, for example, 10-20 ethylene oxide units for o/w emulsifiers and 20-40 ethylene oxide units for the solubilizers. Particularly advantageous o/w emulsifiers for the purposes of the invention are Ceteareth-12 and PEG-20 Stearate.

Nonionic emulsifiers from the group of alkyl oligoglycosides are particularly compatible with the skin (e.g., $C_{8-22}$ alkyl mono- and oligoglycosides, their production and their use being known from the prior art). Such oligoglycosides are produced by reacting glucose or oligosaccharides with primary alcohols containing 8 to 22 carbon atoms. So far as the glycoside component is concerned, both monoglycosides, where a cyclic sugar unit is attached to the fatty alcohol by a glycoside bond, and oligomeric glycosides with a degree of oligomerization of preferably up to about 8, are suitable. The degree of oligomerization is a statistical mean value on which a homolog distribution typical of such technical products is based. Products available under the trademark, PLANTACARE, contain a $C_{8-16}$ alkyl group attached by a glucosidic bond to an oligoglucoside unit with an average degree of oligomerization of 1 to 2. The acyl glucamides derived from glucamine are also suitable nonionic emulsifiers. The product marketed under the trademark, EMULGADE PL 68/50 by Cognis Deutschland GmbH, which is a 1:1 mixture of alkyl polyglucosides and fatty alcohols, may be used.

Natural Active Compounds

Natural active compounds include essential oils. Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° C. to 240° C. and densities ranging from about 0.759 to about 1.096.

Essential oils typically are named by the plant from which the oil is found. For example, rose oil or peppermint oils are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *Eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention. In particular, lavender oil, peppermint oil, and mixtures of lavender oil and peppermint oil are preferred.

Other natural active ingredients, in particular natural active ingredients for the skin may also be included. Non-limiting examples include arginine, lauroyl lysine, phytic acid, citric acid, and mixtures thereof.

Example 1

Formulations

| Formulations | Inventive | | | | | Comparative | | | | |
| --- | --- | --- | --- | --- | --- | --- | --- | --- | --- | --- |
| | 1 | 2 | 3 | 4 | 5 | 6 | 7 | 8 | 9 | 10 |
| Arginine | 3.2 | 3.2 | 3.2 | 2.5 | 2.5 | 3.5 | 3.55 | 3.5 | 3.5 | 3.5 |
| Lauroyl Lysine | 1.5 | 1.5 | 1.5 | 1.5 | 1.5 | | | | | 1.5 |

-continued

|  | Inventive | | | | | Comparative | | | | |
| --- | --- | --- | --- | --- | --- | --- | --- | --- | --- | --- |
| Formulations | 1 | 2 | 3 | 4 | 5 | 6 | 7 | 8 | 9 | 10 |
| Ferulic Acid | 0.25 | 0.25 | 0.25 | 0.25 | 0.25 |  | 0.25 | 0.25 | 0.25 | 0.25 |
| Neohesperidin Dihydrochalcone | 1 | 1 | 1 | 1 | 1 | 1 |  | 1 | 1 | 1 |
| Natural Active Compounds | 0.3 | 0.3 | 0.3 | 0.3 | 0.3 | 0.1 | 0.15 | 0.15 | 0.15 | 0.2 |
| Chromium Oxide | 0.07 | 0.07 | 0.07 | 0.07 | 0.07 |  |  |  |  |  |
| Fatty Compounds | 12.9 | 12.9 | 12.9 | 12.9 | 12.9 | 14.9 | 14.9 | 12.9 | 12.9 | 12.9 |
| Xanthan Gum | 0.2 | 0.2 | 0.2 | 0.2 | 0.2 | 0.2 | 0.2 | 0.2 | 0.2 | 0.2 |
| *Sclerotium* Gum |  | 0.5 |  | 0.5 | 0.5 | 1.2 | 1.2 | 1.2 |  | 0.5 |
| Gellan Gum |  |  | 0.2 |  |  |  |  |  |  |  |
| Chlorphenesin |  |  |  | 0.2 | 0.2 |  |  |  |  |  |
| Water | 40.3 | 39.8 | 40.1 | 40.3 | 40.3 | 55.9 | 56.3 | 50.5 | 46.7 | 44.5 |
| Glycerin (solvent) | 5 | 5 | 5 | 5 | 5 | 5 | 5 | 5 | 5 | 5 |
| Caprylyl Glycol (solvent) | 0.3 | 0.3 | 0.3 | 0.3 | 0.3 | 0.3 | 0.3 | 0.3 | 0.3 | 0.3 |
| 1,3-propanediol (solvent) | 20 | 20 | 20 | 20 | 20 | 3 | 3 | 10 | 15 | 15 |
| Cetearyl Alcohol (and) Cetearyl Glucoside | 6 | 6 | 6 | 6 | 6 | 6 | 6 | 6 | 6 | 6 |
| Glyceryl Stearate | 3 | 3 | 3 | 3 | 3 | 3 | 3 | 3 | 3 | 3 |
| Vegetable Extract (alpha hydroxy acid) | 5 | 5 | 5 | 5 | 5 | 5 | 5.1 | 5 | 5 | 5 |
| Tocopherols | 1 | 1 | 1 | 1 | 1 | 1 | 1 | 1 | 1 | 1 |

The ferulic acid, neohesperidin dihydrochalcone, chromium oxide, xanthan gum, glycerin, caprylyl glycol, and propanediol were combined with water and heated to form an aqueous phase. Separately, cetearyl alcohol (and) cetaryl glucoside, glyceryl stearate, tocopherols, and other fatty compounds were combined and heated to form a fatty phase. The fatty phase was slowly added to the aqueous phase and homogenized for about 15 minutes to form an emulsion. After about 15 minutes, the emulsion was cooled to about 45° C. *Sclerotium* gum in water was added, and the resulting mixture was continuously mixed by maintaining a very low homogenizer speed at a temperature of about 45° C. A separate mixture of vegetable extract (alpha hydroxy acid), arginine, and water was added. Lauroyl lysine was added as a powder. Once hydrated and homogenized to ensure no globules were present, the mixture was de-aerated. If needed, a pH adjuster (such as citric acid or arginine) can be added.

Example 2

Quantification of Anti-Oxidative Potential In-Vivo: Induced Chemiluminescence of Human Skin (ICL-S)

Formulation 4 was evaluated to assess its anti-pollution inhibition. i.e., anti-oxidative potential by in vivo ultraviolate A (UVA) induced chemiluminescence of human skin (ICL-S). This in vivo testing quantifies the antioxidative protection of a topically applied composition. Daily application over a treatment period of two weeks resulted in a significant decrease in ICL-S signal, by about 38% compared to an initial value for Formulation 4. This decrease is statistically significant and confirms the anti-oxidative protection provided by treatment with Formulation 4. The data is presented in the tables below.

|  | Integraded Counting Rate (ICR) | | | |
| --- | --- | --- | --- | --- |
|  |  | Initial Value ($T_0$) | End Value ($T_{2\ weeks}$) | p-Value for Compmarison of Time (vs. $T_0$) |
| Geometric Mean | Untreated area | 101790 | 98542 | Not Signficant |
|  | AO-Standard | 94684 | 63700 | Significant (p ≤0.05) |
|  | Formulation 4 | 104972 | 65014 | Significant (p ≤0.05) |

| Difference to Initial Value (%) at $T_{2\ weeks}$ |  | Untreated Area | −3.2% |
| --- | --- | --- | --- |
|  |  | AO-Standard | −32.7% |
|  |  | Formulation 4 | −38.1% |
|  |  | AO-Standard | −29.5% |
|  | Corrected by Untreated Area | Formulation 4 | −34.9% |

| Comparison of Areas (Differences) | p-Value (vs. Untreated Area) | p-Value (vs. OA-Standard) |
| --- | --- | --- |
| Formulation 4 | Significant (p ≤0.05) | Not Signficant |
| AO-Standard | Significant (p ≤0.05) |  |

Example 3

Antioxidant Activity: Ex-Vivo

The aim of this study was to investigate the ability of Formulation 5 to protect against the damaging effects of air pollution. Cigarette smoke was used to "pollute" skin sebum after it was collected from a volunteer's forehead. The "polluted" skin sebum was then further stressed by UVA (5 J/cm$^2$). "Clean" skin sebum was also collected from the same area of the forehead together with sebum that was subjected to cigarette smoke pollution, and exposed simultaneously under the same UVA dose. Squalene (SQ) and its oxidized products, squalene mono hydroperoxidation (SQOOH), were selected as the analyzing targets in this study, as these targets are well regarded as an indicator of a pollution inhibition effect. The "polluted" skin sebum exhibited a higher oxidation value than the "clean" skin sebum. The inhibition effect of Formulation 5 was determined against bare sebum (sebum from an area of the forehead not treated with Formulation 5). The results, which are graphically presented in FIG. 1, show 76% squalene oxidation inhibition.

Example 4

In Vivo Protective Effect

Figure 2:
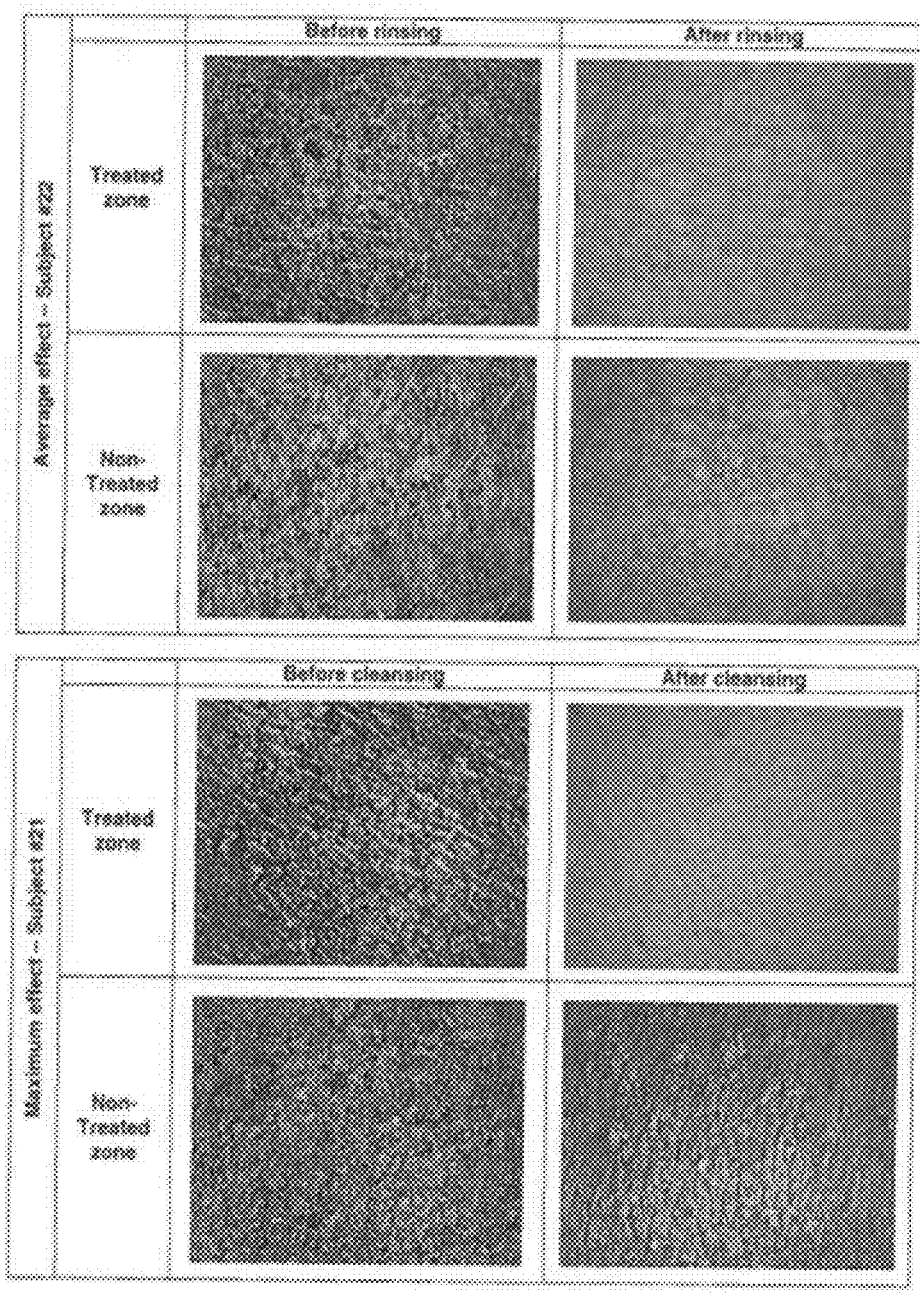
FIG. 2 is an illustration of results from a clinical test evaluating the protective effects of a formulation according to the instant disclosure against atmospheric pollution.

A clinical In-Vivo Dermscan test was conducted to evaluate the protective effects provided against particles representing atmospheric pollution. The testing investigates the adherence of micro-particles (carbon particles) on the skin after treatment (or lack of treatment) with Formulation 4. Skin was treated with Formulation 4 and then subjected to micro-particles representing the carbon particles in atmospheric pollution. Untreated skin was also subjected to the micro-particles. After being subjected to the micro-particles, the skin was cleansed with a standard skin cleanser. After cleansing, the amount of micro-particles remaining on the skin was determined based on imaging using the Hirox© videomicroscope and image analysis (n=25). The results are provided in FIG. 2. The results show that the remaining micro-particles were significantly different between the zones of skin treated with Formulation 4 versus the untreated zones of skin, thereby indicating that formulation 4 provides a significant "protective" effect against atmospheric pollution. The data showed a statistically significant greater decrease in micro-particle quantity for the zone treated with the Formulation 4 versus the non-treated zone.

Example 5

4-Week Open Randomized Clinical Evaluation

The aim of this study was to evaluate the efficacy of Formulation 4 on the facial skin of women after repeated applications for 4 weeks. During the course of the study, subjects applied Formulation 4 to the face, 3 times per week, as directed. Clinical evaluations were conducted at visit 1 (baseline), visit 2 (week 1), and visit 3 (week 4). Subjects participated in the following procedures at each of the time points. The effects of Formulation 4 on the cutaneous characteristics were observed by clinical evaluations, biometrologic measurements, and self-reported subjective evaluations by the users. These observations were performed under normal conditions of use, at different application times. As shown in the table below, the following statistically significant improvements were observed after a 1-week and a 4-week application period of the:

Radiance/luminosity of the skin;

Evenness of the skin tone;

Clarity/translucence of the skin; and

Overall appearance of skin.

| Parameter | Time Point | N | Mean | Mean Change | Mean Change, % | Signed-Rank Test P-value* |
|---|---|---|---|---|---|---|
| Skin clarity/translucency | Baseline | 51 | 4.72 | — | — | — |
|  | Week 1 | 51 | 4.43 | −0.28 | −6.0 | <.001 |
|  | Week 4 | 51 | 4.16 | −0.56 | −11.9 | <.001 |
| Overall appearance | Baseline | 51 | 4.55 | — | — | — |
|  | Week 1 | 51 | 4.41 | −0.14 | −3.0 | <.001 |
|  | Week 4 | 51 | 4.13 | −0.42 | −9.3 | <.001 |
| Radiance/luminosity | Baseline | 51 | 4.71 | — | — | — |
|  | Week 1 | 51 | 4.32 | −0.38 | −8.1 | <.001 |
|  | Week 4 | 51 | 4.05 | −0.66 | −14.0 | <.001 |
| Skin tone evenness | Baseline | 51 | 4.62 | — | — | — |
|  | Week 1 | 51 | 4.55 | −0.07 | −1.5 | 0.016 |
|  | Week 4 | 51 | 4.41 | −0.21 | −4.5 | <.001 |

The data show that Formulation 4 protects the skin from environmental pollutant stressors by providing significant anti-oxidative protection. This protection contributes to the surprising and statistically significant cosmetic improvements to the skin, including radiance/luminosity, evenness of skin tone, clarity/translucence of the skin, and overall appearance of the skin.

Example 6

Stability of Neophesperidin Dihydrochalcone

It was unexpectedly found that a threshold amount of propanediol contributes to surprisingly stable formulations of neophesperidin dihydrochalcone. Experimental trials proved the stability of this antioxidant in typical emulsions and also with many natural ingredients, such as natural actives, natural fatty compounds, and natural vegetable extracts (alpha hydroxy acid). Furthermore, the formulations were stable despite using different polysaccharide gums at various concentrations.

| Formula | ND (Active) | Propanediol | Thickener | Stability |
|---|---|---|---|---|
| Formula 1 | 1% | 20% | 0.5% | No Crystals at 2 Months |
| Formula 2 | 1% | 20% | 0.5% | No Crystals at 2 Months |
| Formula 3 | 1% | 20% | 0.2% | No Crystals at 2 Months |
| Formula 6 | 1% | 3% | 1.2% | Crystals at 24 Hours |

-continued

| Formula | ND (Active) | Propanediol | Thickener | Stability |
|---|---|---|---|---|
| Formula 7 | 0% | 3% | 1.2% | Crystals at 24 Hours |
| Formula 8 | 1% | 10% | 1.2% | Crystals at 24 Hours |
| Formula 9 | 1% | 15% | 0.0% | Crystals at 24 Hours |
| Formula 10 | 1% | 15% | 0.5% | Crystals at 24 Hours |

As shown by the data above, a threshold level of 20% of 1,3-propanediol solubilized and stabilized the neohesperidine dihydrochalcone. Different polysaccharide gums at various levels can be used as thickeners without affecting the solubility and stability of the neohesperidin dihydrochalcone. Furthermore, various fatty alcohols, carbohydrates and emulsifiers can also be used without compromising solubility and stability.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

The term "stable" as used herein means that the composition does not exhibit phase separation and/or visible crystallization.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A topical antioxidant composition comprising:
   (a) at least 0.5 to 3 wt. % of neohesperidin dihydrochalcone;
   (b) about 1 wt. % to about 30 wt. % by weight of one or more of fatty compounds;
   (c) about 0.1 wt. % to about 2 wt. % by weight of one or more natural thickeners;
   (d) at least 20 wt. % 1,3-propanediol;
   (e) about 1 wt. % to about 15 wt. % by weight of one or more emulsifiers;
   (f) optionally, one or more natural active compounds; and
   (g) water;
      wherein the composition is in the form of an emulsion,
      the composition does not exhibit phase separation and/or visible crystallization for at least two months at a temperature of about 25° C.; and
      all percentages by weight are based on the total weight of the composition.

2. The antioxidant composition of claim 1 comprising about 0.9 wt. % to about 1.1 wt. % of neohesperidin dihydrochalcone.

3. The antioxidant composition of claim 1, further comprising ferulic acid.

4. The antioxidant composition of claim 1, further comprising tocopherols.

5. The antioxidant composition of claim 1, further comprising ferulic acid and tocopherols.

6. The antioxidant composition of claim 5, wherein the total amount of the neohesperidin dihydrochalcone, ferulic acid, and tocopherols in the compositions is from about 1% to about 5%.

7. The antioxidant composition of claim 6 comprising about 0.9 wt. % to about 1.1 wt. % of neohesperidin dihydrochalcone.

8. The antioxidant composition of claim 1, wherein the one or more fatty compounds are selected from the group consisting of natural oils of vegetable, animal or marine origin, synthetic oils, mineral oils, hydrogenated oils, silicone oils, hydrocarbon-based compounds, saturated or unsaturated fatty acids, fatty acid esters, liquid waxes, fatty alcohols, and a mixture thereof.

9. The antioxidant composition of claim 8 comprising one or more vegetable oils.

10. The antioxidant composition of claim 1, further comprising 1,2-octanediol.

11. The antioxidant composition of claim 1 comprising glycerin.

12. The antioxidant composition of claim 1, wherein the one or more natural thickeners comprises one or more polysaccharide thickeners.

13. The antioxidant composition of claim 12, wherein the one or more polysaccharide thickeners is selected from the group consisting of gellan gum, xanthan gum, rhamsan gum, welan gum, carrageenan, guar gum, locust bean gum, tragacanth gum, succinoglucan gum, and mixtures thereof.

14. The antioxidant composition of claim 1 comprising one or more emulsifiers selected from the group consisting of stearic acid, cetyl alcohol, PEG-100 stearate and glyceryl stearate, cetearyl glucoside, polysorbate 20, ceteareth-20, cetyl alcohol, cetearyl alcohol, cetyl palmitate, stearyl alcohol, lecithin, hydrogenated lecithin, steareth-2, steareth-20, polyglyceryl-2 stearate, and mixtures thereof.

15. The composition of claim 1, further comprising caprylyl glycol and glycerin.

16. A topical antioxidant composition comprising:
(a) about 0.9 wt. % to about 1.1 wt. % of neohesperidin dihydrochalcone;
(b) about 1 wt. % to about 30 wt. % by weight of one or more of fatty compounds;
(c) about 0.1 wt. % to about 2 wt. % by weight of one or more natural thickeners;
(d) at least 20 wt. % of 1,3-propanediol;
(e) about 5 wt. % to about 15 wt. % of one or more emulsifiers;
(f) optionally, one or more natural active compounds; and
(g) water,
wherein the composition is in the form of an emulsion, the composition does not exhibit phase separation and/or visible crystallization for at least two months at a temperature of about 25° C.; and
all percentages by weight are based on the total weight of the composition.

17. The antioxidant composition of claim 16, further comprising ferulic acid and tocopherols.

18. The composition of claim 16, further comprising caprylyl glycol and glycerin.

19. A method for treating skin conditions resulting from environmental stress and pollution comprising topically applying to the skin area in need of the treatment an antioxidant composition of claim 1.

20. A method for:
(a) improving the radiance of skin;
(b) improving the evenness of skin tone;
(c) improving the clarity of skin; and/or
(d) improving the overall appearance of skin:
comprising applying an antioxidant composition of claim 1 to the skin.

21. The method of claim 20, wherein the skin is facial skin.

* * * * *